(12) United States Patent
Shields

(10) Patent No.: US 8,895,798 B2
(45) Date of Patent: Nov. 25, 2014

(54) METHOD FOR ALTERING AN OPERATION OF AN ALKYLATION UNIT

(75) Inventor: Dale James Shields, Grayslake, IL (US)

(73) Assignee: UOP LLC, Des Plaines, IL (US)

( * ) Notice: Subject to any disclaimer, the term of this patent is extended or adjusted under 35 U.S.C. 154(b) by 931 days.

(21) Appl. No.: 12/478,163

(22) Filed: Jun. 4, 2009

(65) Prior Publication Data

US 2010/0312034 A1 Dec. 9, 2010

(51) Int. Cl.
- C07C 2/56 (2006.01)
- C07C 2/62 (2006.01)
- B01J 19/00 (2006.01)

(52) U.S. Cl.
CPC ...... *B01J 19/002* (2013.01); *B01J 2219/00272* (2013.01); *B01J 2219/00006* (2013.01); *B01J 2219/00162* (2013.01); *B01J 2219/00263* (2013.01); *C07C 2527/1206* (2013.01); *C07C 2/62* (2013.01)
USPC .......................................... 585/719

(58) Field of Classification Search
USPC .......... 585/710, 719, 723, 720; 422/111, 189, 422/187, 188; 203/98
See application file for complete search history.

(56) References Cited

U.S. PATENT DOCUMENTS

| | | | |
|---|---|---|---|
| 3,160,673 A | 12/1964 | Black et al. | |
| 4,046,516 A | 9/1977 | Burton et al. | |
| 4,225,740 A | 9/1980 | Chapman et al. | |
| 4,275,032 A | 6/1981 | Anderson | |
| 4,276,439 A | 6/1981 | Hutson, Jr. et al. | |
| 4,428,759 A * | 1/1984 | Ryan et al. | 62/635 |
| RE32,600 E * | 2/1988 | Ryan et al. | 62/635 |
| 4,774,375 A | 9/1988 | Hammershaimb et al. | |
| 4,797,133 A | 1/1989 | Pujado | |
| 5,098,668 A * | 3/1992 | Callen et al. | 422/111 |
| 5,258,568 A | 11/1993 | Child et al. | |
| 5,407,830 A | 4/1995 | Altman et al. | |
| 5,681,749 A | 10/1997 | Ramamoorthy | |
| 5,811,627 A | 9/1998 | Welsh | |
| 6,187,986 B1 | 2/2001 | Schlaeppi | |
| 6,897,345 B2 | 5/2005 | Marchionna et al. | |
| 2007/0017793 A1 * | 1/2007 | Yao | 203/42 |
| 2008/0177123 A1 | 7/2008 | Blais et al. | |

OTHER PUBLICATIONS

Albright et al., Alkylation of Isobutane with Pentenes Using Sulfuric Acid as a Catalyst: Chemistry and Reaction Mechanisms, Industrial & Engineering Chemistry Research, Feb. 1992, vol. 31, No. 2, pp. 475-481.

Platon et al., Solid Acid Characteristics and Isobutane/Butene Alkylation, Applied Catalysis A: General, Mar. 30, 2005, vol. 282, No. 1-2, pp. 93-100.

Stewart et al., Design Concepts for a Hydrogen Fluoride Emergency De-Inventory System, Process Safety Progress, Apr. 1994, vol. 13, No. 2, pp. 105-107.

* cited by examiner

*Primary Examiner* — In Suk Bullock
*Assistant Examiner* — Sharon Pregler
(74) *Attorney, Agent, or Firm* — James C Paschall

(57) ABSTRACT

One exemplary embodiment can be a method for altering an operation of an alkylation unit during a process upset. The method may include blocking an outlet of a settler to a separation zone, and recycling at least a portion of a hydrocarbon stream to the separation zone to prevent an uncontrolled pressure rise in one or more distillation columns during shutdown of an alkylation reactor.

20 Claims, 2 Drawing Sheets

US 8,895,798 B2

METHOD FOR ALTERING AN OPERATION OF AN ALKYLATION UNIT

FIELD OF THE INVENTION

This invention generally relates to a method for altering an operation of an alkylation unit during a process upset.

DESCRIPTION OF THE RELATED ART

Alkylation process units often incorporate a safety system for quickly removing an alkylation catalyst, which can be an acid alkylation catalyst, from a reactor typically by automated mechanisms. During normal operations, the reactor effluent from a downstream alkylation catalyst settler and/or surge drum may be routed to the first column in the fractionation section. In the event of an emergency, such as a leak, the acid alkylation catalyst from the unit can be removed during a shutdown. Often, the reactor and settler are isolated from a fractionation section when the rapid alkylation catalyst evacuation is initiated by closing a valve on the settler effluent to the fractionation section. However, this effluent may serve as a heat sink by providing most of the reflux of the distillation column. A sudden loss of this effluent can cause the remaining material in the column to vaporize, resulting in an over-pressure in the column. Usually, the pressure relief valves open and communicate this material to a refinery flare. Unfortunately, routing the material to the flare can result in a loss of product. Desirably, it would be beneficial to have an orderly shutdown of the column to prevent over-pressuring and loss of product.

SUMMARY OF THE INVENTION

One exemplary embodiment can be a method for altering an operation of an alkylation unit during a process upset. The method may include blocking an outlet of a settler to a separation zone, and recycling at least a portion of a hydrocarbon stream to the separation zone to prevent an uncontrolled pressure rise in one or more distillation columns during shutdown of an alkylation reactor.

Another exemplary embodiment may be a method for altering an operation of a hydrogen fluoride alkylation unit during a process upset. The method can include recycling at least a portion of an isoparaffin stream to a separation zone. Generally, the separation zone includes at least one distillation column to prevent an uncontrolled pressure rise in that column during shutdown of an alkylation reactor and blocking an outlet of a settler.

Yet a further exemplary embodiment can be a method for altering an operation of a hydrogen fluoride alkylation unit during a process upset. The method can include blocking an outlet of a settler to a separation zone, recycling an isobutane stream to the separation zone to prevent an uncontrolled pressure rise in one or more distillation columns during shutdown of the alkylation reactor, and blocking an olefin stream to an inlet of the alkylation reactor.

The embodiments disclosed herein can allow the recycling of a hydrocarbon stream to the separation zone to prevent uncontrolled pressurization in one or more distillation columns in that zone during shutdown. Usually, the outlet of a settler is blocked and its contents can be routed to one or more storage units to evacuate alkylation catalyst from an alkylation reactor and/or settler. Generally, the embodiments disclosed herein can provide the controlled shutdown of an alkylation unit or system to minimize the amount of material released by the pressure relief system and sent to the flare for disposal. As a consequence, the embodiments herein can minimize product loss.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Additionally, characterizing a stream as, e.g., a "hydrocarbon stream", "isobutane stream" and an "olefin stream" can mean a stream rich in, respectively, at least one hydrocarbon, isobutane, and olefin.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, preferably about 50%, and optimally about 80%, by mole, of a compound or class of compounds in a stream, a feed, or an effluent.

As used herein, the term "vapor" can mean at least one of a gas or a dispersion that may include or consist of one or more hydrocarbons.

As used herein, the term "hydrogen fluoride" can include at least one of a hydrogen fluoride or a hydrofluoric acid. Generally, a hydrofluoric acid is a solution of a hydrogen fluoride in water, where the hydrogen fluoride can disassociate and may form ions of $H_3O^+$, $H^+$, $FHF^-$, and $F^-$.

As depicted, process flow lines in the figures can be referred to as lines, feeds, effluents, or streams. Particularly, a line can contain one or more feeds, effluents, or streams, and one or more feeds, effluents, and streams can be contained by a line.

DETAILED DESCRIPTION

Figure 1:
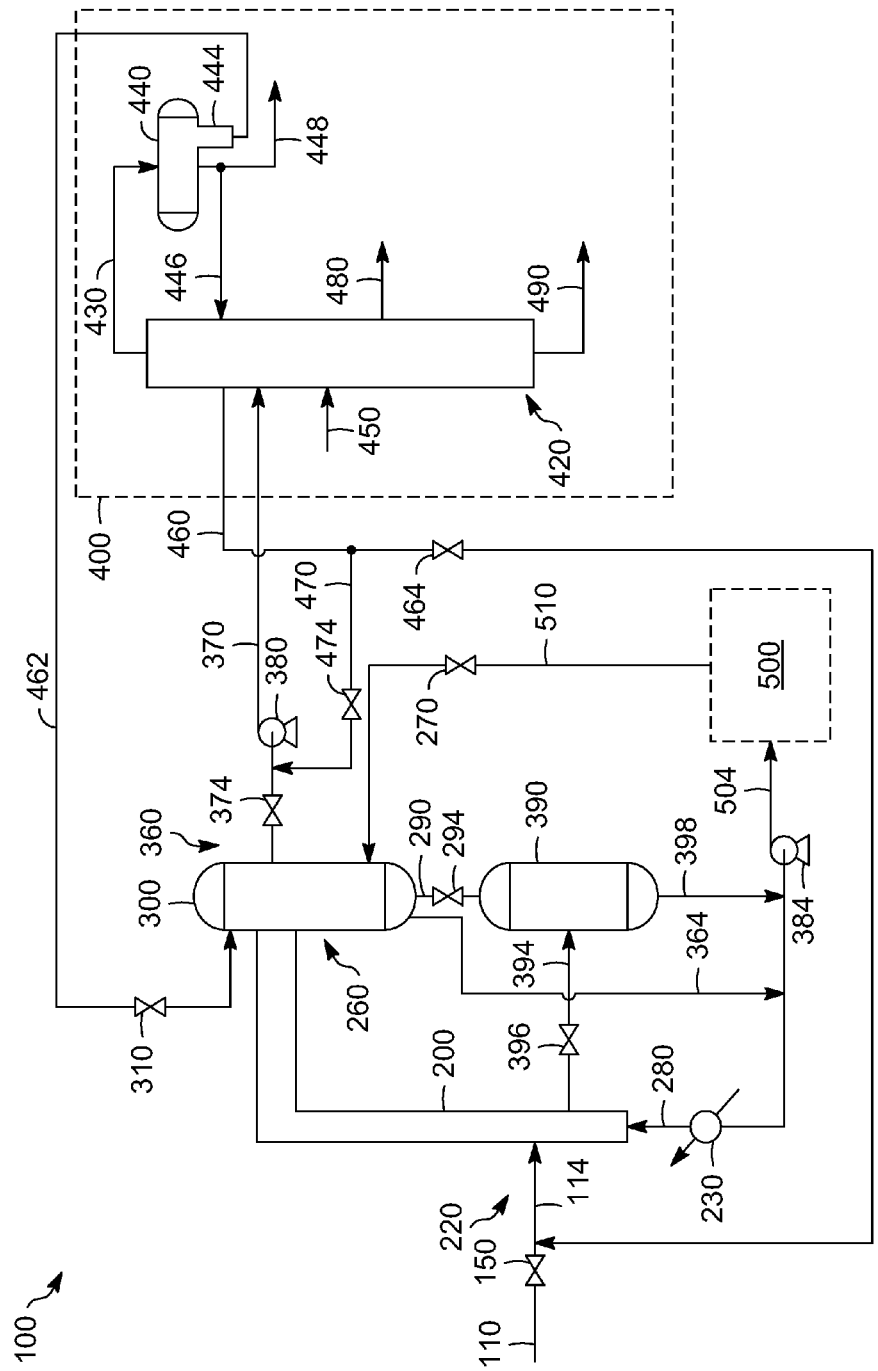
FIG. 1 is a schematic depiction of an exemplary alkylation unit or system.

Referring to FIG. 1, an exemplary alkylation unit or system 100 can include an alkylation reactor 200, a settler 300, an alkylation catalyst storage vessel 390, a separation zone 400, and a regeneration zone 500. The alkylation reactor 200, the settler 300, the alkylation catalyst storage vessel 390, the separation zone 400, and the regeneration zone 500, can be any suitable vessel or zone, such as those disclosed in, e.g., U.S. Pat. No. 5,098,668.

Usually, the alkylation reaction can include the reaction of an isoparaffin, such as isobutane, with an olefin or other alkylating agent such as propylene, isobutylene, butene-1, butenes-2, and amylenes. Generally, the reaction of an isobutane with a C3 or a C4 olefin, such as isobutylene, butene-1, and/or butenes-2, is an example of a preferred reaction involving these specified materials and mixture. Usually, the stream rich in isobutane can at least be partially provided by recycling isobutane from the downstream separation zone 400 and include make-up isobutane from one or more other refinery or chemical manufacturing units.

Typically, the alkylation catalyst can include a hydrogen fluoride, a sulfuric acid, a phosphoric acid, a metal halide, or other suitable alkylation catalyst. Preferably, the catalyst is a hydrogen fluoride. Generally, the alkylation reaction is carried out with substantial molar excess of isoparaffin:olefin, typically in excess of about 1:1, usually about 4:1-about 70:1, preferably about 5:1-about 20:1. Usually, the system or unit 100 can maintain an alkylation catalyst:hydrocarbon volume ratio of about 1:1-about 5:1.

The system or unit 100 may be operated with a volatility reducing agent to improve safety margins in the event of an uncontrolled acid release. The volatility reducing agents normally contemplated are those that may reduce the volatility of the acid alkylation catalyst. The agent may include at least one of an organic sulfone, such as 3-methylsulfolane, 2,4-dimethylsulfolane, and tetramethylenesulfone, which may also be referred to as sulfolane, an ammonia, an amine, such as a lower alkylamine (e.g., methyl to pentyl), a pyridine, an alkylpyridine, a picoline, a melamine, and a hexmethylenetetramine. Exemplary volatility reducing agents are disclosed, in, e.g., US 2008/0177123 A1.

A stream 110 can act as a feed and usually includes one or more olefins and optionally one or more isoparaffins provided separately from one or more other units in a refinery and/or chemical manufacturing facility. Typically, the one or more olefins includes C3 and/or C4 olefins and the one or more isoparaffins can include isobutane. At least a portion of the isobutane can be provided by a hydrocarbon stream 460, which can be recycled from the separation zone 400, as hereinafter described. Optionally, a make-up isoparaffin stream 450 can be provided to one or more distillation columns 420 in the separation zone 400, which is described in further detail hereinafter.

Streams 110 and 460 can pass through respective valves 150 and 464 and be combined as a feed 114 to the alkylation reactor 200. The alkylation reactor 200 can have an inlet 220 and an outlet 260. Also, an alkylation catalyst, such as hydrogen fluoride, can be provided by a stream 280, as hereinafter described. The alkylation reactor 200 may have vertical and horizontal sections, which can have the same diameter. The reaction can continue to the outlet 260, which can also be inlet 260 to the settler 300. The alkylation reactor 200 can be at a pressure of about 100-about 7,000 kPa, preferably about 400-about 1,600 kPa with a residence time of about 10 seconds-about 300 seconds. The temperature of the reaction can vary but usually ranges from about −40-about 70° C. In the reaction of, e.g., an isoparaffin, such as isobutane with a C3 and/or a C4 olefin, the reaction temperature is preferably about 15-about 40° C.

A reaction effluent can exit the alkylation reactor 200 and be provided to the settler 300. The settler 300 can have the inlet 260 and an outlet 360. The settler 300 can operate at a pressure of up to about 1,100 kPa, preferably about 400-about 1,100 kPa. Typically, the settler 300 can provide a hydrocarbon settler effluent 370 from the outlet 360 past a valve 374 to a fluid transfer device 380. The fluid transfer device 380 can be a pump, which may provide the hydrocarbon settler effluent 370 to the separation zone 400.

In addition, the settler 300 can provide an alkylation catalyst via gravity through a line 364. A portion of the alkylation catalyst in the line 364 can be passed through a cooling water exchanger 230 and be provided as the stream 280 to the alkylation reactor 200. Another portion of the alkylation catalyst in the line 364 can be passed via another fluid transfer device 384, such as a pump, to the regeneration zone 500 as a spent alkylation catalyst stream 504. A regenerated alkylation catalyst stream 510 passing through a valve 270 from the regeneration zone 500 can be provided to the settler 300. In addition, the settler 300 can receive an alkylation catalyst in a line 462 passing through a valve 310 from the separation zone 400 recycled to the settler 300, as hereinafter described.

The separation zone 400 can be downstream of the settler 300 and may include one or more distillation columns 420. In this exemplary embodiment, a single distillation column 420 can include a receiver 440 forming a boot 444. The hydrocarbon settler effluent 370 can enter the column 420 and the column 420 may provide an overhead stream 430, a sidestream 480, typically including n-butane, and a bottom stream 490, which typically includes an alkylation product. The overhead stream 430 can be provided to the receiver 440. A portion of a hydrocarbon product, typically a light product such as propane, can be refluxed back to the column as a reflux stream 446 and another portion can be withdrawn as a light product stream 448. Moreover, the column 420 can receive a make-up isoparaffin stream 450, such as an isobutane stream, as discussed above. Furthermore, the alkylation catalyst can be collected in the boot 444 and be recycled back to the settler 300 in a line 462 after passing through the valve 310. Yet another hydrocarbon stream 460 can be withdrawn from the column 420, particularly an isoparaffin stream, e.g., isobutane. During normal operation, the hydrocarbon stream 460 can pass through a valve 464, and optionally with a fluid transfer device, such as a pump, be recycled to the feed 114, as discussed above.

During an upset in the alkylation process, the hydrocarbon stream 460 can be recycled to the distillation column 420 to prevent an inordinate amount of material being sent to the flare. Often during an upset, the alkylation reactor 200 and settler 300 are isolated and material from the settler 300 is blocked from the distillation column 420. Thus, usually a great amount of heat-absorbing material is removed from the column 420. As a result, the remaining hydrocarbons in the column can boil and vaporize, greatly increasing pressure within the column 420. Generally, the one or more safety valves can release this material to the flare, however, this material is then lost. As a consequence, it is beneficial, as described herein, to prevent or at least minimize over-pressuring of the distillation column 420.

If an upset should occur in the alkylation reactor 200 and/or the settler 300, the hydrocarbon stream 460 can be recycled through a line 470. Particularly, the valve 464 can close and a valve 474 can open to route the hydrocarbon stream 460 to the fluid transfer device 380. Subsequently, this material can then be sent to the column 420 to replace the settler effluent 370. As a result, over-pressurizing may be prevented. In addition, other valves can isolate the alkylation reactor 200 and the settler 300. Particularly, the valves 310, 270, and 374 can close to isolate the settler 300 and the valve 150 along with the valve 464 can close to block the feed 114 to the alkylation reactor 200. Namely, closing the valve 270 can prevent the return of regenerated acid from the regeneration zone 500 to the settler 300.

In addition, a valve 294 can open to allow the contents of the settler 300 to pass via a line 290 to the storage vessel 390 while a valve 396 can open to allow the contents of the alkylation reactor 200 to pass via a line 394 to the storage vessel 390. Suitable actuators, controllers, valves, and venting systems can be provided to ensure a relatively rapid evacuation, as disclosed in, e.g., U.S. Pat. No. 5,098,668. The contents of the storage vessel 390 can then be passed through a line 398 to either be recharged to the alkylation reactor 200 and/or the regeneration zone 500.

Figure 2:
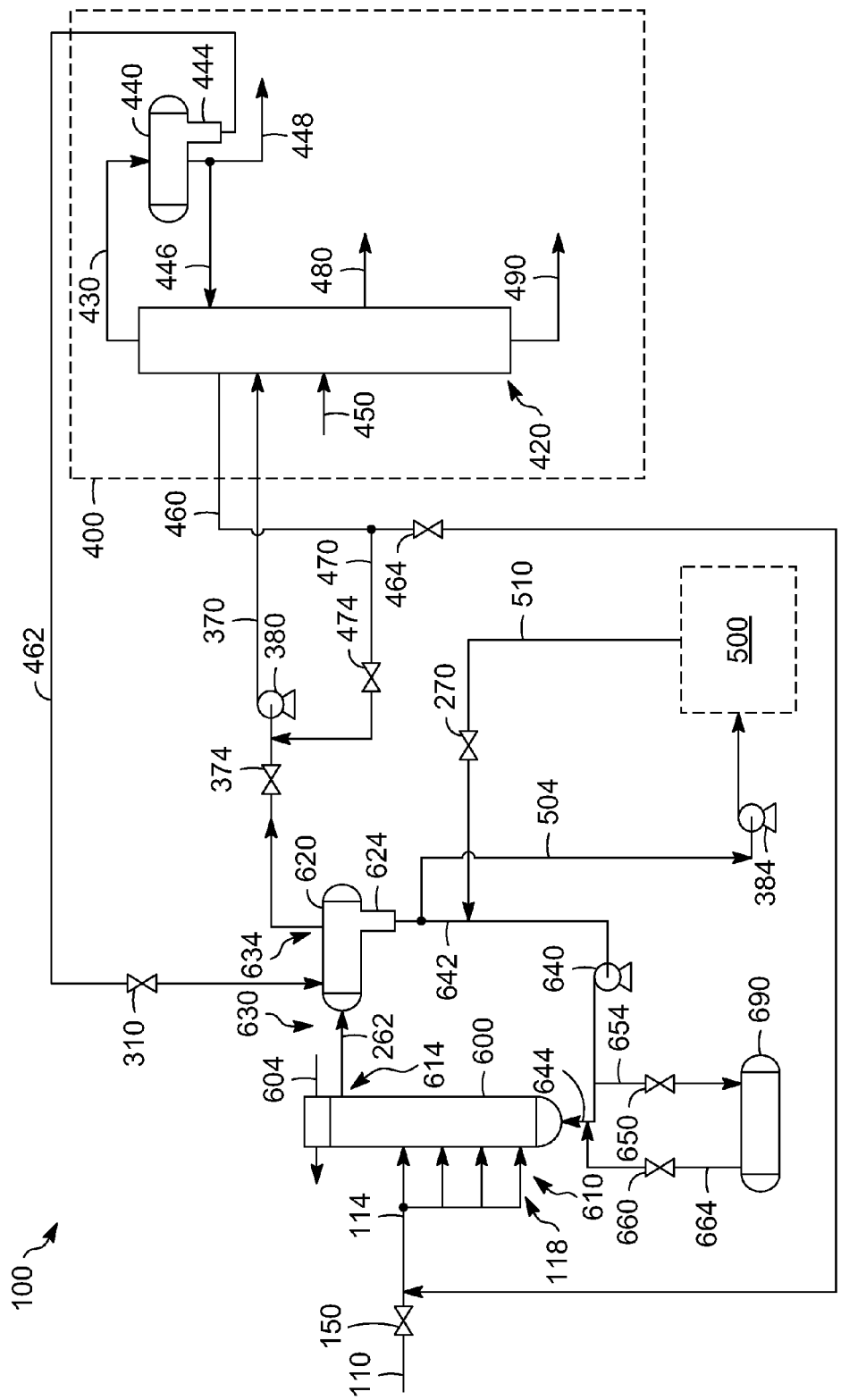
FIG. 2 is a schematic depiction of the alkylation unit or system with another version of at least an alkylation reactor and settler.

Referring to FIG. 2, another exemplary version of the alkylation unit or system 100 is depicted. The alkylation unit or system 100 can include an alkylation reactor 600, such as a cooler-reactor 600, a settler 620, an alkylation catalyst storage vessel 690, a separation zone 400, and a regeneration zone 500. The separation zone 400 and the regeneration zone 500 are substantially the same as discussed above, while the cooler-reactor 600, the settler 620, and the alkylation catalyst storage vessel 690 can have substantially the same function, but vary structurally from the vessels described above. At least some these vessels 600, 620, and 690 are described in, e.g., U.S. Pat. No. 5,098,668. Generally, the cooler-reactor 600 can provide a reaction effluent 262 to the settler 620, and the settler 620 can provide an alkylation catalyst via a fluid transfer device 640, such as a pump, to the cooler-reactor 600 instead of utilizing gravity, as discussed above. Also, the alkylation catalyst storage vessel 690 can be orientated substantially horizontally, instead of vertically as depicted in FIG. 1.

In typical operation, the stream 110 including one or more olefins can be combined with the hydrocarbon stream 460 to form the feed 114. Typically, the feed 114 can pass through one or more lines 118, typically spargers, to enter the cooler-reactor 600. Typically, the cooler-reactor 600 can receive a cooling water stream 604 and receive an alkylation catalyst via line 644, as hereinafter described. The cooler-reactor 600 can have one or more inlets 610 and have an outlet 614. The cooler-reactor 600 may be operated at pressures varying from about 100-about 7,000 kPa, preferably about 600-about 1,600 kPa with a residence time of about 5-about 300 seconds. The temperature of the reaction can vary but usually ranges from about −40-about 70° C. In the reaction of, e.g., an isoparaffin, such as isobutane with a C3 and/or a C4 olefin, the reaction temperature is preferably about 15-about 40° C. The cooler-reactor 600 can provide the reaction effluent 262 via the outlet 614 to the settler 620.

In this exemplary embodiment, the settler 620 may have an inlet 630 and an outlet 634, and form a boot 624. The settler 620 may operate at a pressure up to about 1,500 kPa. Typically, the reaction effluent 262 can be received in the inlet 630 and separate into two or more phases within the settler 620 with a hydrocarbon phase exiting the outlet 634 via the line 370 to the separation zone 400. The acid phase in the reaction effluent 262 can settle in the boot 624 of the settler 620 and be provided via a line 504 to the regeneration zone 500. Usually, a fluid transfer device 384, such as a pump can be utilized. The regeneration zone 500 can then provide the regenerated alkylation catalyst, passing through the valve 270, in the line 510 to a line 642, which can combine with other alkylation catalyst from the boot 624 not sent to the regeneration zone 500. The alkylation catalyst in the line 642 can be provided to the fluid transfer device 640, such as a pump, and then to the cooler-reactor 600 via the line 644. Optionally, make-up alkylation catalyst can be provided from the storage vessel 690 via a line 664 by passing through a valve 660.

During an upset, the hydrocarbon stream 460, usually including an isoparaffin, can be recycled by closing the valve 464 and opening the valve 474, as discussed above. In addition, the valve 374 can also be closed to prevent material from backing into the settler 620. The hydrocarbon stream 460 can then pass through a line 470 to the fluid transfer device 380. Subsequently, this material can be recycled to the column 420 instead of a settler effluent 370. In addition, the cooler-reactor 600 and the settler 620 can be isolated. Particularly, the valve 310 can be closed blocking the alkylation catalyst recycle in the line 462 from the separation zone 400. Moreover, other valves can be closed, such as the valve 150, preventing the hydrocarbon stream 110 from entering the cooler-reactor 600, and the valve 270, preventing regenerated acid from entering the settler 620. The olefins can be introduced by a separate stream than the recycle isoparaffin stream 460, and subsequently mixed with the isoparaffin before being sent to the cooler-reactor 600. At the time the recycle stream 460 is diverted, the olefin feed can be shut-off. In addition, material can be sent to the storage vessel 690 from the cooler-reactor 600 and the settler 620 by opening a valve 650 permitting passage through a line 654, and closing the valve 660 and blocking fluid from entering the cooler-reactor 600 via the line 644 by, e.g., closing a valve.

Thus, the system 100 disclosed herein can provide a method for rapidly moving alkylation catalyst from the vessels while minimizing upsets in downstream fractionation. Thus, a more orderly shutdown or closed circulation operation of the system 100 can be provided to prevent undue upsets in the separation zone 400. Typically, by activating a closed circulation loop, a column 420 hydrocarbon sidestream, typically an isobutane recycle stream 460, can be sent back to the separation zone 400 when the reactor circuit is isolated to activate an alkylation catalyst transfer.

In either version of the system 100 as depicted in the FIGS. 1 and 2, optionally the alkylation catalyst may be dumped from the reactor and/or settler. In one exemplary embodiment, the hydrocarbon stream 460 can only be partially diverted with the remainder flowing to the reactor and/or the settler. So, part may be recycled to maintain a controlled shutdown of the separation zone 400 while another portion may be diverted to the alkylation reactor and/or the settler. Olefin feed can be cut off and the isobutane recycle can be continued to purge the alkylation catalyst content of the reactor and to maintain pressure in the compressor and the settler.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for altering an operation of an alkylation unit during a process upset, comprising:
A) blocking an outlet of a settler to a separation zone during a process upset; and
B) recycling at least a portion of a hydrocarbon side stream to the separation zone to prevent an uncontrolled pressure rise in one or more distillation columns during shutdown of an alkylation reactor, wherein the recycling occurs in response to blocking of the outlet of the settler to the separation zone.

2. The method according to claim 1, wherein the hydrocarbon stream comprises an isoparaffin.

3. The method according to claim 2, wherein the isoparaffin comprises an isobutane.

4. The method according to claim 1, further comprising providing one or more olefins to the alkylation unit.

5. The method according to claim 4, wherein the one or more olefins comprises at least one of a $C_3$ and a $C_4$ olefin.

6. The method according to claim 1, further comprising providing an alkylation catalyst to the alkylation unit.

7. The method according to claim 6, wherein the alkylation catalyst comprises a hydrogen fluoride.

8. The method according to claim 1, further comprising providing an effluent from the alkylation reactor to the settler.

9. The method according to claim 8, wherein the settler returns an alkylation catalyst via gravity to the alkylation reactor.

10. The method according to claim 8, wherein the settler returns an alkylation catalyst via a fluid transfer device to the alkylation reactor.

11. The method according to claim 1, further comprising blocking a stream comprising an alkylation catalyst from the separation zone.

12. The method according to claim 1, further comprising blocking the hydrocarbon stream to an inlet of the alkylation reactor.

13. The method according to claim 1, further comprising opening lines from the alkylation reactor and the settler to an alkylation catalyst storage vessel.

14. The method according to claim 1, further comprising providing a fluid transfer device wherein the hydrocarbon stream is received by the fluid transfer device.

15. The method according to claim 14, wherein the fluid transfer device comprises a pump.

16. A method for altering an operation of a hydrogen fluoride alkylation unit during a process upset, comprising:
   A) recycling at least a portion of an isoparaffin stream taken above feed point to a separation zone comprising at least one distillation column to prevent an uncontrolled pressure rise in that column during shutdown of an alkylation reactor and blocking an outlet of a settler, wherein the recycling occurs in response to blocking of the outlet of the settler during the shutdown.

17. The method according to claim 16, further comprising blocking the isoparaffin stream to an inlet of the alkylation reactor.

18. A method for altering an operation of a hydrogen fluoride alkylation unit during a process upset, comprising:
   A) blocking an outlet of a settler to a separation zone during a process upset;
   B) recycling an isobutane stream to the separation zone to prevent an uncontrolled pressure rise in one or more distillation columns during shutdown of the alkylation reactor; and
   C) blocking an olefin stream to an inlet of the alkylation reactor wherein the recycling occurs in response to blocking of the outlet of the settler to the separation zone.

19. The method according to claim 18, further comprising providing a stream comprising a hydrogen fluoride catalyst to the alkylation reactor via gravity.

20. The method according to claim 18, further comprising providing a stream comprising a hydrogen fluoride catalyst to the alkylation reactor via a fluid transfer device.

* * * * *